(12) United States Patent
McGuckin, Jr. et al.

(10) Patent No.: US 9,510,929 B2
(45) Date of Patent: Dec. 6, 2016

(54) VEIN FILTER

(71) Applicant: Argon Medical Devices, Inc., Plano, TX (US)

(72) Inventors: James F. McGuckin, Jr., Radnor, PA (US); James Erich Bressler, Langhorne, PA (US); David M. Schaller, Wallingford, PA (US)

(73) Assignee: Argon Medical Devices, Inc., Plano, TX (US)

( * ) Notice: Subject to any disclaimer, the term of this patent is extended or adjusted under 35 U.S.C. 154(b) by 52 days.

(21) Appl. No.: 13/913,467

(22) Filed: Jun. 9, 2013

(65) Prior Publication Data

US 2013/0274793 A1    Oct. 17, 2013

Related U.S. Application Data

(63) Continuation-in-part of application No. 13/726,160, filed on Dec. 23, 2012, now Pat. No. 9,168,121, which is a continuation of application No. 11/978,821, filed on Oct. 30, 2007, now Pat. No.

(Continued)

(51) Int. Cl.
*A61F 2/01* (2006.01)
*A61B 17/221* (2006.01)
*A61F 2/848* (2013.01)

(52) U.S. Cl.
CPC .......... *A61F 2/01* (2013.01); *A61B 2017/2215* (2013.01); *A61F 2002/018* (2013.01);
(Continued)

(58) Field of Classification Search
CPC ............... A61F 2/01; A61F 2002/018; A61F 2017/2215; A61F 2230/005; A61F 2/013

USPC ........................................................ 606/200
See application file for complete search history.

(56) References Cited

U.S. PATENT DOCUMENTS 3,744,492 A    7/1973  Leibinsohn
3,952,747 A    4/1976  Kimmell, Jr.
(Continued)

FOREIGN PATENT DOCUMENTS

DE    3429850    2/1986
EP    1894543    3/2008
(Continued)

OTHER PUBLICATIONS

B. Braun Medical, Inc. Vena Tech™ Vena Cava Filters, Feb. 2000.
(Continued)

*Primary Examiner* — Kathleen Holwerda
(74) *Attorney, Agent, or Firm* — IpHorgan Ltd.

(57) ABSTRACT

A vessel filter comprising a first region and a second region wherein the filter is movable between a collapsed position for delivery to the vessel and an expanded position for placement within the vessel. A first region has a filter portion having a converging region to direct particles toward the center of the filter and having a plurality of spaced apart elongated struts and, a plurality of connecting struts extending at an angle from the elongated struts to form closed geometric shapes. The second region is flared in the expanded position to have a transverse dimension increasing toward a second end portion opposite the first end portion. The second region includes vessel engaging hooks at the second end portion. The first region has a plurality of closed looped spacer struts extending radially with respect to a longitudinal axis of the filter when the filter is in the expanded position.

11 Claims, 4 Drawing Sheets

Related U.S. Application Data 8,366,736, which is a continuation of application No. 10/889,429, filed on Jul. 12, 2004, now Pat. No. 7,704,266, which is a continuation-in-part of application No. 10/805,796, filed on Mar. 22, 2004, now Pat. No. 7,338,512, application No. 13/913,467, which is a continuation of application No. 12/319,277, filed on Jan. 5, 2009, now abandoned.

(60) Provisional application No. 60/572,274, filed on May 18, 2004, provisional application No. 60/538,379, filed on Jan. 22, 2004, provisional application No. 61/010,837, filed on Jan. 11, 2008.

(52) U.S. Cl.
CPC *A61F2002/8483* (2013.01); *A61F 2220/0016* (2013.01); *A61F 2230/005* (2013.01); *A61F 2230/008* (2013.01); *A61F 2250/0059* (2013.01)

(56) References Cited

U.S. PATENT DOCUMENTS

| | | |
|---|---|---|
| 4,266,815 A | 5/1981 | Cross |
| 4,425,908 A * | 1/1984 | Simon .................. 128/899 |
| 4,494,531 A | 1/1985 | Gianturco |
| 4,512,338 A | 4/1985 | Balko et al. |
| 4,619,246 A | 10/1986 | Molgaard-Nielsen et al. |
| 4,643,184 A | 2/1987 | Mobin-Uddin |
| 4,688,553 A | 8/1987 | Metals |
| 4,727,873 A | 3/1988 | Mobin-Uddin |
| 4,781,177 A | 11/1988 | Lebigot |
| 4,793,348 A | 12/1988 | Palmaz |
| 4,817,600 A | 4/1989 | Herms et al. |
| 4,832,055 A * | 5/1989 | Palestrant .................. 128/899 |
| 4,957,501 A | 9/1990 | Lahille et al. |
| 4,990,156 A | 2/1991 | Lefebvre |
| 4,994,069 A | 2/1991 | Ritchart et al. |
| 5,059,205 A | 10/1991 | El-Nounou et al. |
| 5,108,418 A | 4/1992 | Lefebvre |
| 5,133,733 A | 7/1992 | Rasmussen et al. |
| 5,152,777 A | 10/1992 | Goldberg et al. |
| 5,234,458 A | 8/1993 | Metals |
| 5,300,086 A | 4/1994 | Gory et al. |
| 5,324,304 A | 6/1994 | Rasmussen |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,531,788 A | 7/1996 | Dibie et al. |
| 5,591,197 A | 1/1997 | Orth et al. |
| 5,601,595 A | 2/1997 | Smith |
| 5,626,605 A | 5/1997 | Irie et al. |
| 5,634,942 A | 6/1997 | Chevillon et al. |
| 5,681,347 A | 10/1997 | Cathcart et al. |
| 5,683,411 A | 11/1997 | Kavteladze et al. |
| 5,690,671 A | 11/1997 | McGurk et al. |
| 5,704,910 A | 1/1998 | Humes |
| 5,709,704 A | 1/1998 | Nott et al. |
| 5,725,552 A | 3/1998 | Kotula et al. |
| 5,733,294 A | 3/1998 | Forber et al. |
| 5,733,329 A | 3/1998 | Wallace et al. |
| 5,746,767 A | 5/1998 | Smith |
| 5,755,779 A | 5/1998 | Horiguchi |
| 5,755,790 A | 5/1998 | Chevillon et al. |
| 5,776,162 A | 7/1998 | Kleshinski |
| 5,782,748 A | 7/1998 | Palmer et al. |
| 5,795,322 A | 8/1998 | Boudewijn |
| 5,800,457 A | 9/1998 | Gelbfish |
| 5,810,874 A | 9/1998 | Lefebvre |
| 5,836,968 A | 11/1998 | Simon et al. |
| 5,853,420 A | 12/1998 | Chevillon et al. |
| 5,893,869 A | 4/1999 | Barnhart et al. |
| 5,895,398 A | 4/1999 | Wensel et al. |
| 5,895,410 A | 4/1999 | Forber et al. |
| 5,911,717 A | 6/1999 | Jacobsen et al. |
| 5,938,683 A | 8/1999 | Lefebvre |
| 5,968,071 A | 10/1999 | Chevillon et al. |
| 5,976,172 A | 11/1999 | Homsma et al. |
| 5,984,947 A | 11/1999 | Smith |
| 6,007,558 A | 12/1999 | Ravenscroft et al. |
| 6,013,093 A | 1/2000 | Nott et al. |
| 6,042,598 A | 3/2000 | Tsugita et al. |
| 6,059,825 A | 5/2000 | Hobbs et al. |
| 6,063,113 A | 5/2000 | Kavteladze et al. |
| 6,066,158 A | 5/2000 | Engelson et al. |
| 6,080,178 A | 6/2000 | Meglin |
| 6,093,196 A | 7/2000 | Okada |
| 6,093,199 A | 7/2000 | Brown et al. |
| 6,096,052 A | 8/2000 | Callister et al. |
| 6,099,549 A | 8/2000 | Bosma et al. |
| 6,117,154 A | 9/2000 | Barbut et al. |
| 6,123,715 A | 9/2000 | Amplatza |
| 6,126,673 A | 10/2000 | Kim et al. |
| 6,146,404 A | 11/2000 | Kim et al. |
| 6,152,946 A | 11/2000 | Broome et al. |
| 6,165,179 A | 12/2000 | Cathcart et al. |
| 6,165,198 A | 12/2000 | McGurk et al. |
| 6,168,579 B1 | 1/2001 | Tsugita |
| 6,168,603 B1 | 1/2001 | Leslie et al. |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,187,025 B1 | 2/2001 | Machek |
| 6,193,739 B1 | 2/2001 | Chevillon et al. |
| 6,214,025 B1 | 4/2001 | Thistle et al. |
| 6,217,600 B1 | 4/2001 | DiMatteo |
| 6,231,581 B1 | 5/2001 | Shank et al. |
| 6,231,589 B1 | 5/2001 | Wessman et al. |
| 6,235,044 B1 | 5/2001 | Root et al. |
| 6,235,045 B1 | 5/2001 | Barbut et al. |
| 6,241,746 B1 | 6/2001 | Bosma et al. |
| 6,245,012 B1 | 6/2001 | Kleshinski et al. |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,901 B1 | 8/2001 | Whitcher et al. |
| 6,280,451 B1 | 8/2001 | Bates et al. |
| 6,280,457 B1 | 8/2001 | Wallace et al. |
| 6,290,721 B1 | 9/2001 | Heath |
| 6,328,755 B1 | 12/2001 | Marshall |
| 6,331,183 B1 | 12/2001 | Suon |
| 6,331,184 B1 | 12/2001 | Abrams |
| 6,342,062 B1 | 1/2002 | Suon et al. |
| 6,342,063 B1 | 1/2002 | Devries et al. |
| 6,344,041 B1 | 2/2002 | Kupiecki et al. |
| 6,355,051 B1 | 3/2002 | Sisskind et al. |
| 6,368,338 B1 | 4/2002 | Konya et al. |
| 6,383,205 B1 | 5/2002 | Samson et al. |
| 6,391,045 B1 | 5/2002 | Kim et al. |
| 6,402,771 B1 | 6/2002 | Palmer et al. |
| 6,436,120 B1 | 8/2002 | Meglin |
| 6,436,121 B1 | 8/2002 | Blom |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,468,290 B1 | 10/2002 | Weldon et al. |
| 6,482,222 B1 | 11/2002 | Bruckheimer et al. |
| 6,506,205 B2 | 1/2003 | Goldberg et al. |
| 6,517,559 B1 | 2/2003 | O'Connell |
| 6,527,962 B1 | 3/2003 | Nadal |
| 6,537,294 B1 | 3/2003 | Boyle et al. |
| 6,540,767 B1 | 4/2003 | Walak et al. |
| 6,551,342 B1 | 4/2003 | Shen et al. |
| 6,562,058 B2 | 5/2003 | Sequin et al. |
| 6,589,265 B1 | 7/2003 | Palmer et al. |
| 6,599,307 B1 | 7/2003 | Huter et al. |
| 6,605,102 B1 | 8/2003 | Mazzocchi et al. |

(56) References Cited

U.S. PATENT DOCUMENTS

| | | |
|---|---|---|
| 6,620,183 B2 | 9/2003 | DiMatteo |
| 6,652,558 B2 | 11/2003 | Patel et al. |
| 6,656,202 B2 | 12/2003 | Papp et al. |
| 6,660,021 B1 | 12/2003 | Palmer et al. |
| 6,695,878 B2 | 2/2004 | McGuckin et al. |
| 6,706,054 B2 | 3/2004 | Wessman et al. |
| 6,783,538 B2 | 8/2004 | McGuckin et al. |
| 6,793,665 B2 | 9/2004 | McGuckin et al. |
| 6,890,340 B2 | 5/2005 | Duane |
| 6,932,831 B2 | 8/2005 | Forber |
| 6,958,074 B2 | 10/2005 | Russell |
| 6,972,025 B2 | 12/2005 | WasDyke |
| 6,989,021 B2 | 1/2006 | Bosma et al. |
| 6,994,092 B2 | 2/2006 | Va der Burg et al. |
| 7,011,094 B2 | 3/2006 | Rapacki et al. |
| 7,037,321 B2 | 5/2006 | Sachdeva et al. |
| 7,097,651 B2 | 8/2006 | Harrison et al. |
| 7,232,462 B2 | 6/2007 | Schaeffer |
| 7,279,000 B2 | 10/2007 | Cartier et al. |
| 7,316,708 B2 | 1/2008 | Gordon et al. |
| 7,338,512 B2 | 3/2008 | McGuckin, Jr. et al. |
| 7,534,251 B2 | 5/2009 | WasDyke et al. |
| 7,572,289 B2 | 8/2009 | Sisken et al. |
| 7,704,266 B2 | 4/2010 | Thinnes et al. |
| 7,867,245 B2 | 1/2011 | Neeman et al. |
| 7,875,018 B2 | 1/2011 | Tockman et al. |
| 7,998,164 B2 | 8/2011 | Saholt et al. |
| 8,029,529 B1 | 10/2011 | Chanduszko |
| 2002/0058911 A1 | 5/2002 | Gilson et al. |
| 2002/0193827 A1 | 12/2002 | McGuckin et al. |
| 2002/0193828 A1 | 12/2002 | Griffin et al. |
| 2003/0065345 A1 | 4/2003 | Weadock |
| 2003/0130680 A1 | 7/2003 | Russel |
| 2003/0195555 A1 | 10/2003 | Khairkhahan et al. |
| 2003/0208227 A1 | 11/2003 | Thomas |
| 2003/0208253 A1 | 11/2003 | Beyer et al. |
| 2004/0044361 A1 | 3/2004 | Frazier et al. |
| 2004/0073252 A1 | 4/2004 | Goldberg et al. |
| 2004/0093017 A1 | 5/2004 | Chanduszko |
| 2004/0158273 A1 | 8/2004 | Weaver et al. |
| 2004/0186510 A1 | 9/2004 | Weaver |
| 2004/0186556 A1 | 9/2004 | Hogendijk et al. |
| 2004/0215230 A1 | 10/2004 | Frazier et al. |
| 2004/0230220 A1 | 11/2004 | Osborne |
| 2005/0004596 A1 | 1/2005 | McGuckin et al. |
| 2005/0015111 A1 | 1/2005 | McGuckin et al. |
| 2005/0027314 A1 | 2/2005 | WasDyke |
| 2005/0043757 A1 | 2/2005 | Arad et al. |
| 2005/0165441 A1 | 7/2005 | McGuckin et al. |
| 2005/0165442 A1 | 7/2005 | Thinnes et al. |
| 2005/0182439 A1 | 8/2005 | Lowe |
| 2005/0234503 A1 | 10/2005 | Ravenscroft et al. |
| 2005/0251199 A1 | 11/2005 | Osborne et al. |
| 2005/0267514 A1 | 12/2005 | Osborne et al. |
| 2005/0267515 A1 | 12/2005 | Oliva et al. |
| 2005/0277977 A1 | 12/2005 | Thornton |
| 2005/0288704 A1 | 12/2005 | Cartier et al. |
| 2006/0030875 A1 | 2/2006 | Tessmer |
| 2006/0058832 A1 | 3/2006 | Melzer et al. |
| 2006/0079928 A1 | 4/2006 | Cartier et al. |
| 2006/0079930 A1 | 4/2006 | McGuckin, Jr. et al. |
| 2006/0095068 A1 | 5/2006 | WasDyke et al. |
| 2006/0100660 A1 | 5/2006 | Osborne et al. |
| 2006/0106417 A1 | 5/2006 | Tessmer et al. |
| 2006/0149295 A1 | 7/2006 | Fleming |
| 2006/0167490 A1 | 7/2006 | Kusleika et al. |
| 2006/0178695 A1 | 8/2006 | Decant et al. |
| 2006/0206138 A1 | 9/2006 | Eidenschink |
| 2007/0005095 A1 | 1/2007 | Osborne et al. |
| 2007/0032816 A1 | 2/2007 | O'Connell et al. |
| 2007/0088381 A1 | 4/2007 | McGuckin, Jr. et al. |
| 2007/0167974 A1 | 7/2007 | Cully et al. |
| 2007/0173885 A1* | 7/2007 | Cartier et al. ............... 606/200 |
| 2007/0198050 A1 | 8/2007 | Ravenscroft et al. |
| 2007/0213685 A1 | 9/2007 | Bressler et al. |
| 2008/0188887 A1 | 8/2008 | Batiste |
| 2008/0221609 A1 | 9/2008 | McGuckin, Jr. |
| 2008/0275486 A1 | 11/2008 | Dwyer et al. |
| 2010/0049238 A1 | 2/2010 | Simpson |
| 2010/0049239 A1 | 2/2010 | McGuckin et al. |
| 2010/0063535 A1 | 3/2010 | Bressler et al. |
| 2010/0106178 A1 | 4/2010 | Obermiller et al. |

FOREIGN PATENT DOCUMENTS

| | | |
|---|---|---|
| WO | WO-9312723 | 7/1993 |
| WO | WO-9509567 | 4/1995 |
| WO | WO-9925252 | 5/1999 |
| WO | WO-0110342 | 2/2001 |
| WO | WO 01/15630 | 3/2001 |
| WO | WO-0145590 | 6/2001 |
| WO | WO 0158381 | 8/2001 |
| WO | WO-0162184 | 8/2001 |
| WO | WO-0172239 | 10/2001 |
| WO | 0211812 | 2/2002 |
| WO | WO 0232496 | 4/2002 |
| WO | WO 02/102436 | 12/2002 |
| WO | WO-03063732 | 8/2003 |
| WO | WO-2004049973 | 6/2004 |
| WO | 2006/036457 | 4/2006 |
| WO | 2006/117750 | 12/2006 |

OTHER PUBLICATIONS

Gianturco-Roehm, Bird's Nest® Vena Cava Filter.

Cordis Corporation, TrapEase™ Permanent Vena Cava Filter, "A Small, Easy and Versatile System for Optimal Pulmonary Emboli Prevention", 2000 (4 pages).

* cited by examiner

FIG_2A

VEIN FILTER

This application is a is a continuation-in-part of prior application Ser. No. 13/726,160, filed Dec. 23, 2012, which is a continuation of prior application Ser. No. 11/978,821, filed Oct. 30, 2007, now U.S. Pat. No. 8,366,736, which is a continuation of application Ser. No. 10/889,429, filed on Jul. 12, 2004, now U.S. Pat. No. 7,704,266, which claims priority from provisional application Ser. No. 60/572,274, filed may 18, 2004, and is a continuation-in-part of application Ser. No. 10/805,796 filed Mar. 22, 2004, now U.S. Pat. No. 7,338,512, which claims priority from provisional application Ser. No. 60/538,379, filed Jan. 22 , 2004, and this application is also a continuation of prior application Ser. No. 12/319,277, filed Jan. 5, 2009, which claims priority from provisional application Ser. No. 61/010,837, filed Jan. 11, 2008. The entire contents of each of these applications are incorporated herein by reference.

BACKGROUND

Technical Field

This application relates to a vascular filter and more particularly to a vein filter for capturing blood clots within the vessel.

Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anti-coagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. To this end, minimally invasive surgical techniques have been developed involving the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832, 055and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Several factors have to be considered in designing vein filters. One factor is that the filter needs to be securely anchored within the vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

The filters disclosed in the commonly assigned co-pending application Ser. No. 10/889,429 (hereinafter "the '429 application"), the entire contents of which are incorporated herein by reference, satisfy the foregoing parameters. The filters have sufficient anchoring force to retain the filter within the vessel while providing atraumatic contact with the vessel wall, have a minimized insertion (collapsed) profile to facilitate delivery through the vascular system to the surgical site, and direct migration of the captured blood clots to the center of the vessel. The filters also provide simplified insertion through the femoral or the right jugular vein or arm into the inferior vena cava.

The filters of the '429 application can advantageously be readily removed minimally invasively, e.g. intravascularly, from the patient, thus advantageously providing for a temporary filter. Thus, these filters advantageously strike the balance of having structure to provide sufficient anchoring while enabling atraumatic removal from the vessel after a period of time. Certain filters of the '429 application also advantageously have a retrieval end configured to facilitate grasping by a snare as well as to facilitate withdrawal by providing a smooth transition into a retrieval sheath.

The filters of the '429 are very effective in achieving their desired functions, whether used as a permanent or temporary filter. The filter of commonly assigned U.S. application Ser. No. 11/888,929, filed Aug. 3, 2007, discloses a modification to the filters of the '429 patent to further facilitate removal if used as a temporary filter. This is achieved by providing spacers at an end of the filter.

It would be advantageous to provide a filter with improved spacers to keep the retrieval end spaced from the vessel wall to thereby further facilitate removal of the filter.

SUMMARY

The present invention provides a vessel filter comprising a first, second and third region. The filter is movable between a collapsed position for delivery to the vessel and an expanded position for placement within the vessel. The first region has a filter portion having a converging region to direct particles toward the center of the filter and includes a plurality of spaced apart elongated struts and a plurality of connecting struts extending at an angle from the elongated struts to form closed geometric shapes. The second region in the expanded position has a transverse dimension increasing toward a second end portion opposite the filter portion and includes vessel engaging hooks at the second end portion. The second end portion is at the proximal region of the filter. The third region has a plurality of closed looped spacer struts extending radially with respect to a longitudinal axis of the filter in the expanded position.

In the preferred embodiment, a transverse dimension of the filter at the region of the looped struts is less than a transverse dimension of the filter at the region of the vessel engaging hooks.

The spacer struts are preferably formed integrally with the filter. In a preferred embodiment, the filter is formed from a laser cut tube composed of shape memory material.

In a preferred embodiment, the converging region terminates in a tubular portion, with each of the elongated struts in the first region extending outwardly from the tubular portion, and the spacer struts extending radially from the tubular portion and positioned distally of the elongated struts (with respect to the direction of blood flow). The spacer struts preferably have a looped shape memory position and during delivery have a collapsed position substantially aligned with the tubular portion. In one embodiment, the loops form arcuate outer surfaces forming an onion type shape. In an alternate embodiment, the loops form wing shapes which bend inwardly toward the distal end of the filter.

The present invention also provides vessel filter comprising a body made from a single tube, the tube cut to create a plurality of integral elongated struts. The struts terminate in vessel engaging hooks at a proximal portion. A second portion of the tube forms an integral filter portion, and a plurality of integral closed wing-shaped looped struts are positioned distally of the filter portion. Each loop extends a distance from a central longitudinal axis of the filter that is less than a distance the vessel engaging hook is from the central longitudinal axis.

The filter preferably includes interconnecting struts in the filtering region of the body to form closed geometric shapes. A wall of the filter preferably separates the looped struts from the filter portion.

A retrieval hook is preferably positioned distally of the looped struts.

In one embodiment, the looped struts form substantially U-shaped loops. In another embodiment, each of the looped struts is wing shaped such that loops extend in a first direction and extend back in a second direction opposite the first direction.

The present invention also provides a vessel filter comprising a tubular portion and a plurality of elongated struts extending integrally from the first portion and curving outwardly therefrom. The struts terminate in integrally formed vessel engaging hooks at a proximal end portion. An intermediate portion of the tube forms a filter portion, and a plurality of closed looped struts are positioned distally of the filter portion and formed integrally with the elongated struts. Each loop extends a distance from a central longitudinal axis of the filter that is less than a distance the vessel engaging hook is from the central longitudinal axis.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Turning now to the drawings, wherein like reference numerals identify similar or like components throughout the several views, the vein filters of the present invention are described for placement within the inferior vena cava to capture blood clots or other particles which could otherwise pass to the lungs.

The filter is movable from a low profile collapsed configuration to facilitate insertion through the delivery sheath to a larger expanded placement configuration to enable atraumatic engagement with the vessel walls to secure (mount) the filter within the inferior vena cava. The filter is preferably substantially bell-shaped and preferably has a flared or mounting region (portion/section) and a filtering region (portion/section). The filtering region has inwardly directed struts, terminating in a converging region, thereby directing particles toward the central axis of the filter. By directing the particles to the center, they will be exposed to greater blood flow (since there is greater flow at the center than near the wall of the vessel) which improves dissolution of the particles. The filter increases in transverse dimension to form a flared region. The flare provides less contact area than a straight region, resulting in less tissue ingrowth to facilitate removal of the filter if desired. The flare also reduces the chance of vessel distortion if inserted into a curved vena cava. The filter also has a third region having spacers positioned distally (with respect to the direction of blood flow) of the filtering region to space the cranial end of the filter from the vessel wall to facilitate removal.

Figure 1:
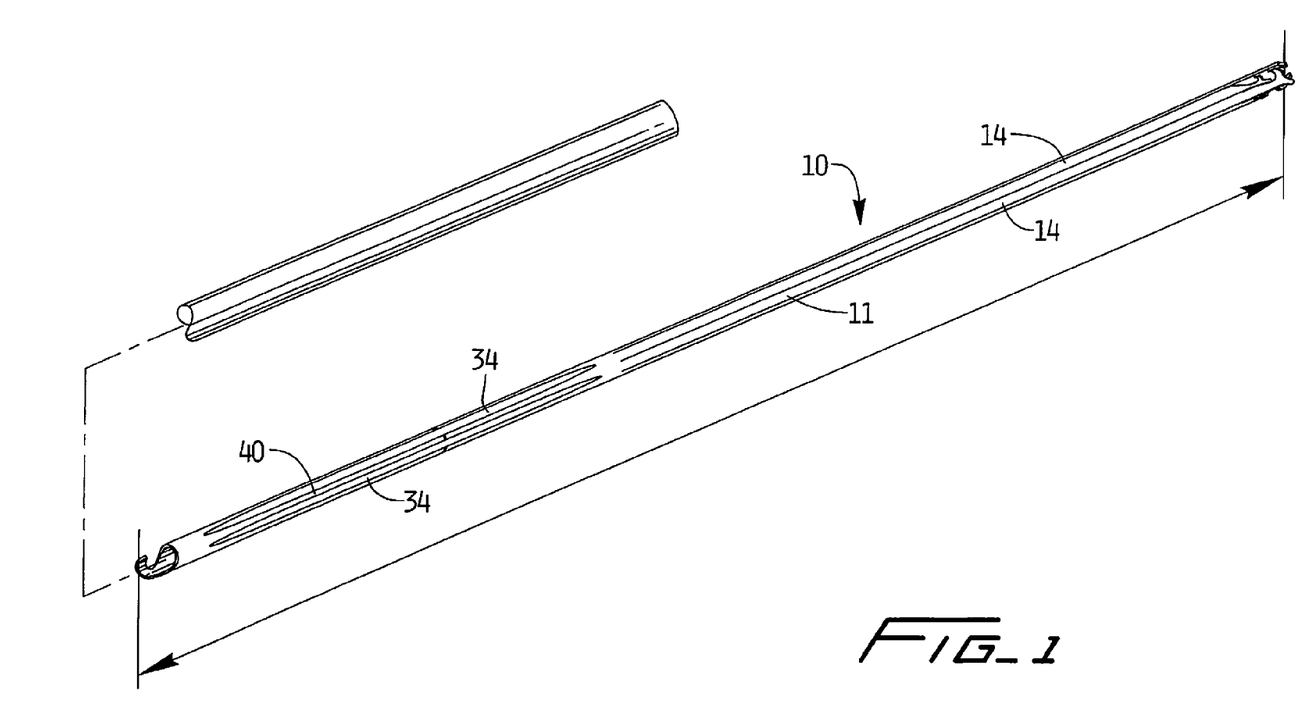
FIG. 1 is a perspective view of a first embodiment of the vein filter of the present invention in the collapsed (retracted) configuration, and shown removed from a delivery tube/sheath.

Turning now to details of the filter of the present invention and with initial reference to FIG. 1, the filter is designated generally by reference numeral 10 and is shown in a collapsed configuration for delivery. Filter 10 is preferably formed from a single tube 11 such that the struts and portions of the filter are integrally formed. In a preferred embodiment, the filter tube 11 is composed of shape memory material, such as Nitinol, a nickel titanium alloy, or elgiloy, however, other materials such as stainless steel are also contemplated. A plurality of cutouts are formed in the filter 10, preferably by laser cutting although other techniques are contemplated. In the illustrated embodiment, six elongated cutouts are formed, creating six strips or struts 14 of substantially uniform width separated by the cutouts. A second plurality of cutouts 34 are formed, forming the spacer struts described in detail below.

The collapsed configuration of filter 10 reduces the overall profile to facilitate delivery to the site. The diameter or transverse dimension of filter 10 in the collapsed configuration is preferably about 2 mm and more preferably about 1.7 mm. Other dimensions are also contemplated. The filter is thus preferably dimensioned for insertion through a 6 French delivery system and through a 6 French catheter. The diameter or transverse dimensions of the filter in the expanded placement configurations (e.g. FIG. 2 is greater than the diameter or transverse dimension in the collapsed (delivery) configuration of FIG. 1.

Figure 2:
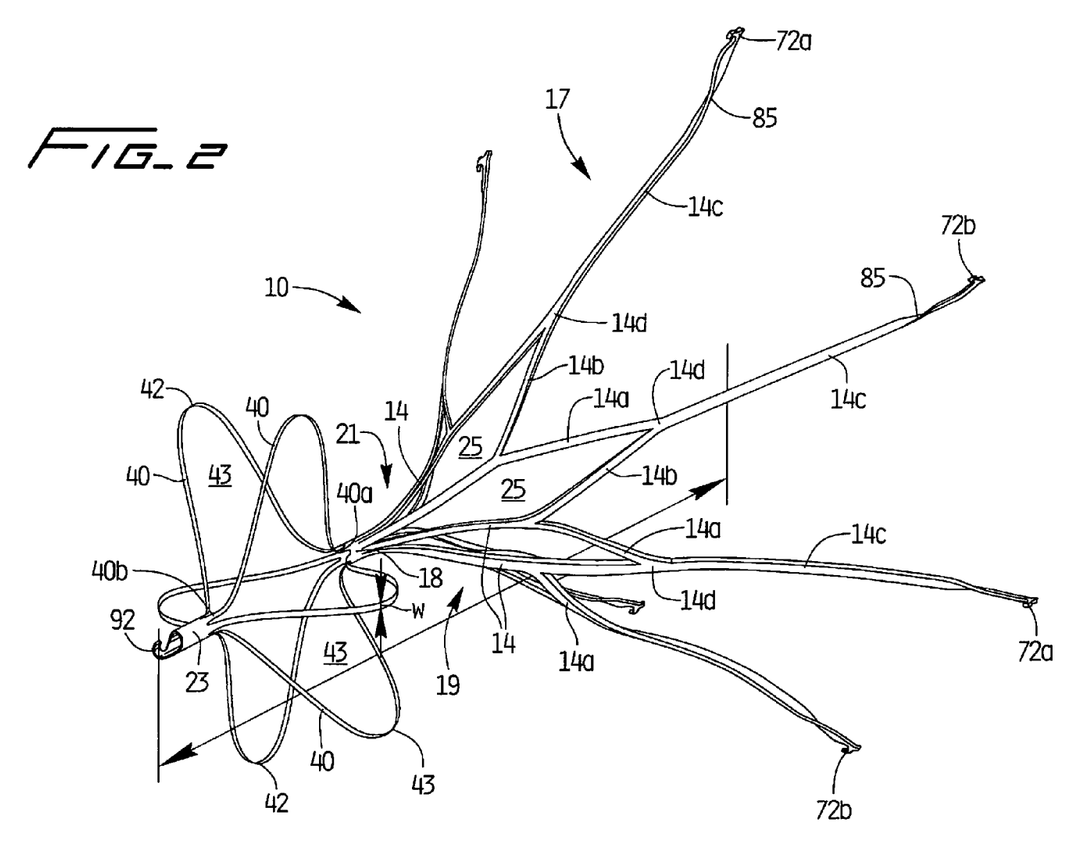
FIG. 2 is a perspective view of the vein filter of FIG. 1 in an expanded (radially extending) configuration.

FIG. 2 illustrates the expanded placement configuration of the filter 10. Filter 10 is generally bell-shaped in configuration. Filter 10 has a flared region 17 and a converging region 21 at the filtering section 19. The transverse dimension of the filter at the flared (or mounting/anchoring) region 17 is greater than the transverse dimension at filtering section 19. Diameters (or transverse dimensions) preferably range from about 18 mm to about 32 mm, depending on the internal diameter of the vessel wall as will be explained in more detail below. Other dimensions are also contemplated. The elongated struts 14 are spaced apart as shown and extend at an angle away from the longitudinal axis L of filter 10 in region 17 to provide a flare. Preferably, this angle or taper is about 8°, although other dimensions are contemplated. When expanded, the six struts 14, as shown, are preferably spaced approximately 60 degrees apart. It is also contemplated that a fewer or greater number of struts and spacing other than 60 degrees could be provided.

Filtering section 19 extends from the flared region 17, and extends toward the central longitudinal axis of the filter 10 and converges into tubular portion 18.

The struts 14 of filter 10 terminate in hooks 72a, 72b which extend substantially perpendicular from the strut, achieved by torquing the struts at the region 85 so the hooks bend out of the plane. A first set of hooks 72a is larger than a second set of hooks 72b (see FIG. 2A). Preferably when formed in a laser cut tube, hooks 72a are formed so that they occupy a region equivalent to the transverse dimension of two adjacent struts. Smaller hooks 72b are spaced axially with respect to each other and axially inwardly with respect to larger hooks 72a as in the filter hooks of the '429 application to minimize the collapsed profile (transverse dimension) of the filter when collapsed for insertion. The penetrating tips 76a, 76b of hooks 72a, 72b, respectively, penetrate the tissue to retain the filter, preferably temporarily, and point distally, toward the cranial (or distal with respect to blood flow) end of the filter.

Figure 2A:
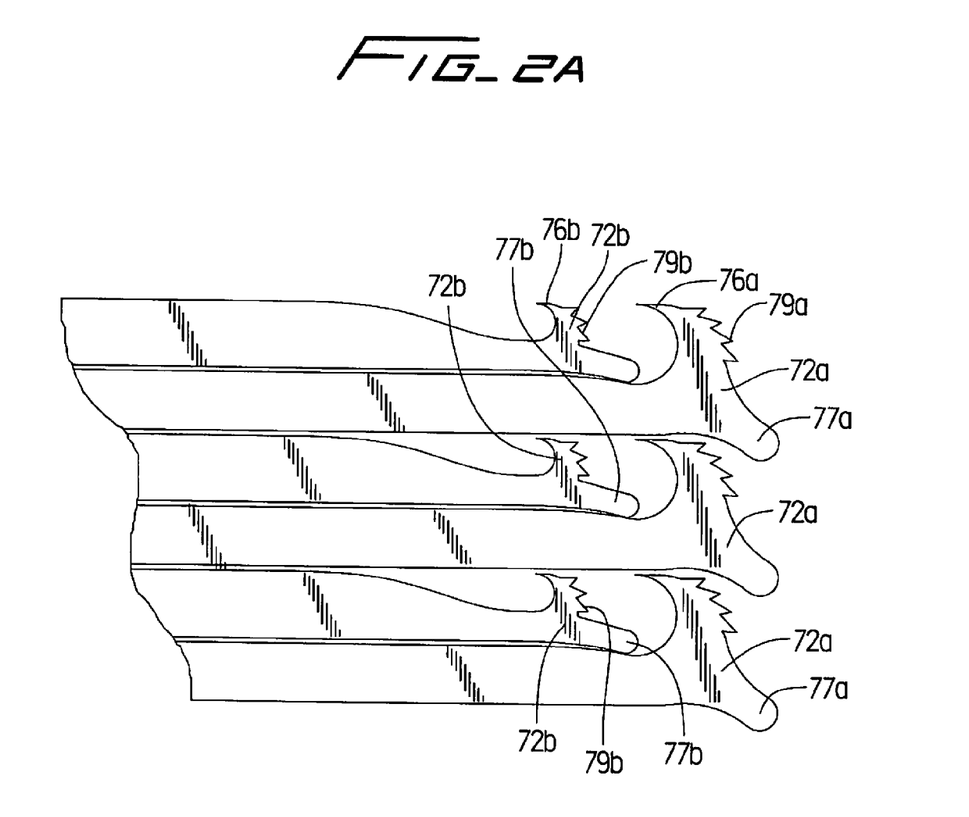
FIG. 2A is an enlarged view of the hooks of the filter of FIG. 2.

Each of the hooks 72a, 72b preferably has a series of teeth 79a, 79b, and a heel 77a, 77b extends past (proximally or caudal of) the respective hook 72a, 72b to function as a stop to prevent the filter strut portions from going through the vessel wall. For clarity, not all of the hooks are fully labeled. This hook configuration is described in detail in commonly assigned patent application Ser. No. 11/888,929, filed Aug. 3, 2007, the entire contents of which is incorporated herein by reference The six filter struts or strut portions 14 curve outwardly from tubular portion 18, extend integrally and radially therefrom and divide into two connecting filter struts or strut portions 14a, 14b (preferably of equal width, although differing dimensions are contemplated) that angle way from each other (in different directions) to extend to the connecting strut portion of an adjacent strut 14. Thus, connecting strut portion 14a of one strut 14 interconnects with the connecting strut portion 14b of an adjacent strut at joining region 14d. This forms closed geometric shapes 25, preferably substantially diamond shaped in configuration. For clarity, not all of the identical parts are labeled in the drawing.

In the illustrated embodiment, preferably six struts are provided forming twelve interconnecting struts, however a different number of struts and closed geometric shapes can be provided. Note that although all six struts 14 are shown interconnected, it is also contemplated that fewer than all the struts can be interconnected. Also, the strut width can vary as described with respect to the filters disclosed in the '429 application.

After convergence of strut portions 14a, 14b at joining region 14d, it transitions into elongated integrally extending mounting strut portions 14c which form flared mounting or anchoring region 17. The length of the strut portions 14c in the anchoring region 17 can vary, with increased/decreased length increasing the flexibility/rigidity of the struts. The thickness of the strut portions can also vary to affect flexibility/rigidity.

As in the other embodiments described in the '429 application, terms such as interconnected, joined, etc., are used for ease of description, it being understood that preferably these portions are integral as they are preferably formed from a single tube. Also, mounting struts and filter struts used to describe the various embodiments disclosed herein can be considered as mounting strut "portions" or "sections" and filter strut "portions" or "sections" of the same struts if the filter is formed integrally, e.g. from a cut tube.

The tubular portion 23 is spaced distally (with respect to the direction of blood flow) of tubular portion 18 and is at the cranial end of filter 10. Tubular portion 23 preferably terminates in retrieval hook 92 as described with respect to the embodiment of FIG. 20 in the '429 application. Other retrieval structure can also be utilized. Hook 92 is described briefly below.

A plurality of slots are formed in a third region of the tube during manufacture, preferably by laser cutting, to enable six strips to be formed creating spacers 40 for the filter at the cranial portion. In the collapsed position, spacers 40 are in a substantially aligned position with respect to tubular portions 18 and 23, i.e. substantially flush with the tubular portions. The tubular portions 18, 23 (and 118, 123 described below) are configured and dimensioned to receive a guidewire therethrough for inserting the filter over a guidewire. Spacers 40 are maintained in this collapsed position during delivery to the surgical site. (see e.g. FIG. 1). The spacers 40 have a shape memorized position forming closed loops being substantially U-shaped shown in FIG. 2 extending radially from the filter. Thus, once exposed from the delivery sheath, the spacers 40 self expand as they move from their collapsed position to their shape memory looped position of FIG. 2. One or more of the curved surfaces 42 of the loops 40 can engage the vessel wall to maintain centering of the cranial end of the filter and to space tubular portion 23 and retrieval hook 92 away from the vessel wall. This spacing limits tissue ingrowth around the hook, thereby making it easier to grasp and remove filter 10.

The loops of spacers 40 are closed loops with end 40a extending from tubular wall 18 and end 40b extending from tubular wall 23. As shown, the looped struts 40 are positioned distally of the filter portion and proximally of the hook 92, with respect to the direction of blood flow and internal integrally from tubular portion 18. In the expanded, shape memorized position shown in FIG. 2, the loop extends such that its apex, i.e. the region at the height of the loop, is generally in the middle portion of the loop 40. Thus, these substantially symmetrical spacer loops extend, when viewed from tubular wall 23, initially radially outwardly and then radially inwardly. An opening 43 through the loop 40 is transverse to the longitudinal axis of the filter.

Each loop 40 preferably has a thickened portion (not shown) at the region adjacent the tubular walls (portions) 18 and 23 to increase the strength at the transition. Also, the loops are preferably rectangular in cross-section, having a width W greater than its height. Although six loops are shown approximately 60 degrees apart, different distances apart are also contemplated. Also, a fewer or greater number could be provided so long as they achieve the spacing function.

A transverse dimension of the looped region is less than a transverse dimension of the mounting (anchoring) region. Stated another way, in the expanded configuration, the distance from the apex of the loop 40 to the central longitudinal axis is lees than the distance from the vessel engaging hook 72a or 72b to the central longitudinal axis.

Figure 3:
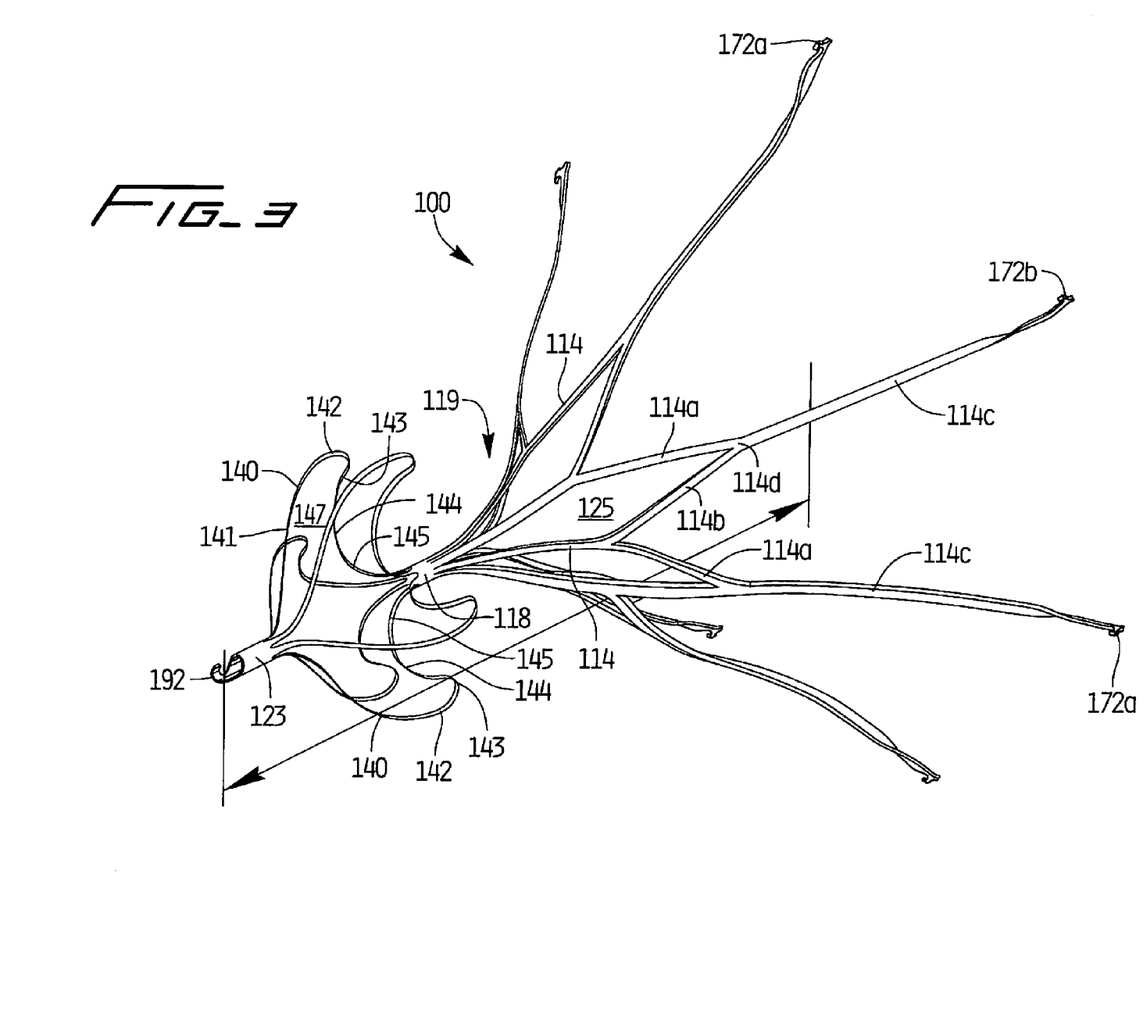
FIG. 3 is a perspective view of an alternate embodiment of the vein filter of the present invention shown in an expanded (radially extending) configuration.

In the alternate embodiment of FIG. 3, filter 100 is identical to filter 10 except for the radially extending spacers 140 (The corresponding parts are labeled in the "100" series). The spacers 140 are in the form of closed loops. Preferably six loops are provided, positioned about 60 degrees apart, although other spacing and other number of loops could be provided. The spacer loops 140 are positioned distal of the filter portion 119 and proximal of the tubular portion 123 and retrieval hook 192 with respect to the direction of blood flow. Preferably they are formed integral with the filter.

The loops 140 are wing shaped such that a distal region 141 extends outwardly and radially in a direction toward the mounting portion (or caudal end) of the filter, reaches an apex region 142 and then bows inwardly at region 143 to extend at region 144 toward the retrieval end (or cranial end) of the filter, forming an inwardly bowed section, and then extends proximally at region 145 into the tubular portion 118. Thus, as shown, the loops 140 point in a direction toward the retrieval end of the filter.

To enable movement between an expanded and collapsed configuration, the filter of the embodiments described herein, as noted above, is preferably made of shape memory metal material, such as Nitinol, a nickel titanium alloy, and preferably manufactured from a laser cut tube. To facilitate passage of the filter through the lumen of the delivery sheath and into the vessel, cold saline is injected into the delivery sheath or catheter and around the filter in its collapsed position within the delivery sheath. This shape memory material characteristically exhibits rigidity in the austenitic state and more flexibility in the martensitic state. The cold saline maintains the temperature dependent filter in a relatively softer condition as it is in the martensitic state within the sheath. This facilitates the exit of the filter from the sheath as frictional contact between the filter and the inner surface of the sheath would otherwise occur if the filter was maintained in a rigid, i.e. austenitic, condition.

Once ejected from the delivery sheath or catheter, the filter is no longer cooled and is exposed to the warmer body temperature, which causes the filter to return towards its austenitic memorized configuration.

In the placement (expanded) configuration, the filter moves towards its memorized position and the extent it returns to its fully memorized position will be dependent on the size of the vessel in which the filter is inserted. (The larger the vessel, the closer the filter comes to returning to its fully memorized position). The extent of movement of the spacer(s) to its fully memorized position could also be limited by the size of the vessel.

The filter can be inserted through the jugular vein in the neck of the patient or through the femoral vein in the leg of the patient or the arm. The filters can also be placed in the superior vena cava.

FIGS. 13-15 of the '929 application illustrate delivery and placement of the filter 10, by way of example, in the inferior vena cava. The filters 10 and 100 disclosed herein can be inserted in the same manner. The delivery catheter is withdrawn to enable filter 10 to be warmed by body temperature to transition to the expanded placement configuration. The other filters described herein could be inserted in the same manner. Note it is implanted in the orientation such that filter section 19 is downstream of the flared section 17. This enables blood clots or other particles to be directed to the center of the filter section by the angled struts. Thus the direction of insertion, e.g. upstream or downstream direction, will determine how the filter is to be positioned in the delivery catheter. Also note in its implanted orientation, spacers 40 (or 140) are downstream of the filter section 19.

The foregoing filters can be removed from access through the internal jugular or femoral vein. Various methods can be used to remove the filter such as those described in commonly assigned co-pending application Ser. No. 11/801,547, filed May 10, 2007 and application Ser. No. 10/889,429, filed Jul. 12, 2004, the entire contents of each of these applications is incorporated herein by reference. Methods include for example, slotted hooks, graspers, etc.

A recess or cutout is preferably provided at the tubular end portion to form a hook portion 90 (FIG. 1) and 190 (FIG. 2). The curved hook 92 or 192 at the proximalmost end receives a snare or other device for removal and is described in detail in the Ser. No. 10/889,429 application incorporated herein by reference in its entirety. The hook 92 as shown in laterally offset from a central longitudinal axis of the filter. This facilitates passages of a guidewire through the filter.

When the filter is grasped by the retrieval device and pulled distally to disengage from the vessel walls, the spacers flex inwardly to collapse within the retrieval sheath or catheter for removal. When the filter is pulled into the retrieval sheath it is collapsed for removal.

To facilitate removal of the filter from the vessel, cold saline can be injected onto the implanted filter to change the temperature of the filter to move it to a relatively softer condition to facilitate the filter being drawn into the retrieval sheath. That is, injection of cold saline will cause the filter to approach its martensitic state, bringing the filter to a more flexible condition. The flexible condition facilitates the collapse and withdrawal of the filter into the retrieval sheath by decreasing the frictional contact between the filter and the inner surface of the retrieval sheath.

A delivery system which can be used for the filter of the present invention which includes a filter cartridge, is shown and described in the Ser. No. 10/889,429 application.

While the above description contains many specifics, those specifics should not be construed as limitations on the scope of the disclosure, but merely as exemplifications of preferred embodiments thereof. For example, the foregoing filters can be inserted in other regions of the body. Also, the foregoing filters can be made of materials other than shape memory material. Those skilled in the art will envision many other possible variations that are within the scope and spirit of the disclosure as defined by the claims appended hereto.

What is claimed is:

1. A vessel filter comprising a single filtering region, a second mounting region and a third region, the filter having a body having a longitudinal axis and a first plurality of elongated cutouts extending longitudinally and a second plurality of cutouts extending longitudinally, the second plurality of cutouts axially spaced from the first plurality of cutouts and being in the third region, the filter movable from a collapsed position having a first transverse dimension to an expanded position having a second transverse dimension larger than the first transverse dimension, in the expanded position the mounting region having a larger transverse dimension than the filtering region, the filter including a first plurality of elongated struts which in the expanded position of the filter are spaced apart and extend at an angle from the longitudinal axis and converge at the filtering region in to a first tubular portion, and a second plurality of struts, the filter further including a second tubular portion axially spaced from the first tubular portion and positioned at a cranial end of the filter, the first plurality of elongated struts being integral with the first tubular portion and the second plurality of struts being integral with the first and second tubular portions, the first plurality of struts are flush with the first and second tubular portions in the collapsed position of the filter such that a transverse dimension of a region of the filter encompassing the first plurality of struts is the same as a transverse dimension of the first and second tubular portions, the first and second tubular portions joined by the second plurality of struts such that the second plurality of struts separates the first and second tubular portions and the first tubular portion is interposed and thereby forms a connecting portion between cranial ends of the first plurality of struts and caudal ends of the second plurality of struts, the second plurality of struts forming spacers having spaced apart closed loops of the same configuration to space the second tubular portion from a vessel wall, the loops extending generally in radial and axial directions and being radially spaced such that the loops are non-overlapping in an axial direction, the loops being wing shaped such that a first region extends outwardly and radially from the second tubular portion toward the mounting region to an apex and then bows inwardly to extend toward the cranial end and then extends toward a caudal end of the filter, the inwardly bowed region forming a concave region between the apex and the first tubular portion, the concave region facing toward the caudal end of the filter.

2. The vessel filter of claim 1, wherein the second plurality of struts are substantially aligned with the first plurality of struts in the collapsed position of the filter.

3. The vessel filter of claim 1, wherein the first and second tubular portions are dimensioned to receive a guidewire therethrough.

4. The vessel filter of claim 1, wherein the loops are self expanding upon exposure from a delivery sheath.

5. The vessel filter of claim 1, wherein the first and second plurality of struts are formed of shape memory material.

6. The vessel filter of claim 1, wherein the first plurality of struts includes vessel engaging members in the mounting region, the loops extending a distance from the longitudinal axis which is less than a distance the vessel engaging members extend from the longitudinal axis.

7. The vessel filter of claim 1, wherein in the expanded configuration an opening in the loops is transverse to the longitudinal axis of the filter.

8. The vessel filter of claim 1, wherein the filter includes retrieval structure at the cranial end and extending from the second tubular portion, the retrieval structure includes a hook laterally offset from a central longitudinal axis of the filter.

9. The vessel filter of claim 1, wherein the loops converge and terminate at the first tubular portion and converge and terminate at the second tubular portion.

10. The vessel filter of claim 1, wherein the loops have a generally flat surfaced vessel engaging portion.

11. The vessel filter of claim 1, wherein the first and second tubular portions have openings extending therethrough and wherein the first and second plurality of strut do not pass through the openings.

* * * * *